United States Patent
Lange et al.

(10) Patent No.: US 9,410,944 B2
(45) Date of Patent: Aug. 9, 2016

(54) METHODS OF ASSAYING SENSITIVITY OF CANCER STEM CELLS TO THERAPEUTIC MODALITIES

(71) Applicant: The Research Foundation for The State University of New York, Albany, NY (US)

(72) Inventors: Christopher S. Lange, Manhasset, NY (US); Bozidar Djordjevic, Westfield, NJ (US); Marvin Z. Rotman, King Point, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 0 days.

(21) Appl. No.: 14/597,735

(22) Filed: Jan. 15, 2015

(65) Prior Publication Data
US 2015/0132792 A1    May 14, 2015

Related U.S. Application Data

(62) Division of application No. 12/594,056, filed as application No. PCT/US2008/004247 on Mar. 31, 2008, now Pat. No. 8,936,938.

(60) Provisional application No. 61/036,739, filed on Mar. 14, 2008, provisional application No. 60/920,922, filed on Mar. 30, 2007.

(51) Int. Cl.
*G01N 33/50* (2006.01)
*C12N 5/00* (2006.01)
*G01N 33/574* (2006.01)

(52) U.S. Cl.
CPC .......... *G01N 33/5011* (2013.01); *C12N 5/0062* (2013.01); *G01N 33/574* (2013.01); *C12N 2502/1323* (2013.01); *C12N 2503/02* (2013.01); *G01N 2800/52* (2013.01)

(58) Field of Classification Search
CPC ................................................ G01N 2800/52
See application file for complete search history.

(56) References Cited

U.S. PATENT DOCUMENTS

| 4,959,301 A | 9/1990 | Weaver et al. |
| 2003/0119080 A1 | 6/2003 | Mangano |
| 2010/0062481 A1 | 3/2010 | Lange et al. |

OTHER PUBLICATIONS

Djordjevic B. et al., "Cell-Cell Interactions in Spheroids Maintained in Suspension". Acta Oncologica 45:412-420 (2006).
Sasaki T. et al., "Development of Multicellular Spheroids of HeLa Cells Cocultured With Fibroblasts and Their Response to X-Irradiation", Cancer Research 44:345-351 (Jan. 1984).
Zhang S-L et al., "Isolation and Characterization of Cancer Stem Cells from Cervical Cancer HeLa Cells", Cytotechnology 64:477-484 (2012).
U.S. non-Final Office Action dated Mar. 18, 2014 issued in corresponding U.S. Appl. No. 12/594,056.
U.S. Final Office Action dated Dec. 28, 2012 issued in corresponding U.S. Appl. No. 12/594,056.
U.S. non-Final Office Action dated Aug. 20, 2012 issued in corresponding U.S. Appl. No. 12/594,056.
International Search Report dated Jun. 20, 2008 issued in corresponding Application No. PCT/US08/04247.

*Primary Examiner* — Bin Shen
(74) *Attorney, Agent, or Firm* — Scully, Scott, Murphy & Presser, P.C.

(57) ABSTRACT

The present invention is directed to methods of measuring the proliferative ability of individual patient cancer stem cells. The present invention provides a method for treating a cancer patient according to an assay of the individual patient's tumor's cancer stem cell sensitivity, by measuring the proliferative ability of cancer stem cells from the patient. By the methods of the present invention it is possible to treat individual cancer stem cells presented in tumor cells. Methods of detecting and enumerating cancer stem cells in hybrid spheroids comprised of fibroblasts and tumor cells are also provided by the present invention. The present invention also contemplates a method for drug and other treatment development, wherein the effects of a drug or combination of drugs or other treatments are determined on the individual patient's cancer stem cells.

2 Claims, 6 Drawing Sheets

METHODS OF ASSAYING SENSITIVITY OF CANCER STEM CELLS TO THERAPEUTIC MODALITIES

CROSS REFERENCE TO RELATED APPLICATIONS

The present application is a divisional of application having U.S. Ser. No. 12/594,056, filed on Nov. 3, 2009, issued as U.S. Pat. No. 8,936,938 on Jan. 20, 2015, which is a 371 of International Application having Serial No. PCT/US08/04247, filed on Mar. 31, 2008, which claims benefit of U.S. Provisional Application No. 61/036,739, filed on Mar. 14, 2008 and U.S. Provisional Application No. 60/920,922, filed on Mar. 30, 2007, the contents of all of which are incorporated herein by reference.

FIELD OF THE INVENTION

The present invention is related to methods of measuring the proliferative ability of single cancer stem cells. Specifically, the present invention is related to methods for measuring the proliferative ability of an individual patient's cancer stem cells by obtaining a single cell suspension from the patient's tumor, engulfing them in a manner that yields an average of a single cancer stem cell in a spheroid of fibroblasts, and assaying the proliferative ability of the cancer stem cells.

BACKGROUND OF THE INVENTION

It is well established that many normal tissues are maintained and regenerated by a small subset of pluri- (or toti-) potential stem cells (SC) [Weismann, A F L. *Das Keimplasma*. G. Fischer, Jena, 1892; Dubois, F., *C. R. Seances Soc Biol et ses Filiales (Paris)* 1948, 142:699-700; Dubois S. F et al., *C. R. Seances Soc Biol et ses Filiales (Paris)* 1960, 155: 115-118; Till J. E et al., *Radiat Res* 1961, 14: 213-222; Till J. E. et al., *Proc Natl Acad Sci USA* 1964, 51: 29-36; Lange C. S et al., *Int J Radiat Biol.* 1968; 14: 373-388; Lange C. S., *Exp Geronto* 1968; 3: 219-230; Wheldon T. E. et al., *Br J Radiol.* 1982, 55: 759; Lajtha L. G., Stem Cell Concepts In: *Stem Cells, Their Identification and Characterization.* Ch. 1, pp 1-11 (Ed. C S Potten) Churchill Livingstone, London, 1983; Lange, C. S., Stem cells in planarians. In: *Stem Cells, Their Identification and Characterization.* Ch. 3, pp 28-66 (Ed. C S Potten) Churchill Livingstone, London, 1983; Wheldon T. E. et al., *Br J Cancer* 1986, 53: 382-385; Morrison S. J et al., *Immunity* 1994, 1: 661-673; Lanzkron S. M. et al., *Blood* 1999, 93: 1916-1921; Osawa M. et al., *Science* 1996, 273: 242-245; Bhatia M. et al., *Nat Med* 1998, 4: 1038-1045; Yilmaz O. H. et al., *Blood* 2006, 107(3): 924-930; Kiel M. J. et al., *Cell* 2005, 121: 1109-1121; Kuperwasser C. et al., *Proc Natl Acad Sci USA* 2004, 101: 4966-4971; Proia D. et al., *Nature Protocols* 2006, 1: 206-214; Stingl J. et al., *Nature* 2006, 439: 993-997]. This also holds for human breast development, which can be recapitulated from an organoid and fibroblast mixture in which the former represents 1% or less of the cells [Kuperwasser C. et al., *Proc Natl Acad Sci USA* 2004, 101: 4966-4971; Proia D. et al., *Nature Protocols* 2006, 1: 206-214; Stingl J. et al., *Nature* 2006, 439: 993-997]. However, stem cell identification is still problematic as the marker combinations which purportedly identify prospective hematopoietic stem cells (the best characterized) label a larger fraction (~2-fold) of cells than that which can repopulate the bone marrow (the functional endpoint) [Yilmaz O. H. et al., *Blood* 2006, 107(3): 924-930; Kiel M. J. et al., *Cell* 2005, 121: 1109-1121]; for breast, the fraction is 100-fold [Al-Hajj M. et al., *Proc Natl Acad Sci USA* 2003, 100: 3983-3988].

The Cancer Stem Cell (CSC) Hypothesis postulates that cancer stem cells 1% or less of the tumor), initially derived from normal tissue stem cells, are necessary for long-term tumor growth and survival and that their eradication is a necessary and sufficient condition for cure [Lajtha L. G., Stem Cell Concepts In: *Stem Cells, Their Identification and Characterization.* Ch. 1, pp 1-11 (Ed. C S Potten) Churchill Livingstone, London, 1983; Al-Hajj M. et al., *Proc Natl Acad Sci USA* 2003, 100: 3983-3988; Dick J. E., *Proc Natl Acad Sci USA* 2003, 100: 3547-3549; Kuperwasser C. et al., *Cancer Res* 2005, 65: 6130-6138; Jordan C. T., *Curr Opinion Cell Biol* 2004, 16: 708-712; Bonnet D. et al., *Nat Med* 1997, 3: 730-737; Singh S. K. et al., *Cancer Res* 2003, 63: 5821-5828]. This suggestion is not new [Lajtha L. G., Stem Cell Concepts In: *Stem Cells, Their Identification and Characterization.* Ch. 1, pp 1-11 (Ed. C S Potten) Churchill Livingstone, London, 1983]. Lajtha noted that an organism's cells can be considered to fall into one of three categories (static, transit and stem), the first two of which have no or little proliferative future. The "cell population type which is self-maintaining with extensive proliferation capacity and persists in the body long enough to be compatible with the time scale of carcinogenesis, and therefore satisfies the criteria of being the main potential target for carcinogens, is the stem cell" [Lajtha L. G., Stem Cell Concepts In: *Stem Cells, Their Identification and Characterization.* Ch. 1, pp 1-11 (Ed. C S Potten) Churchill Livingstone, London, 1983]. Since stem cells can represent less than 0.5% of the total tissue, and DNA synthesis is an error-prone event, it is an excellent strategy for the minimization of cancer risk for most of the divisions to be done by the amplifying transit cells which are soon eliminated. Lajtha further noted that most of the tumor's cells are no longer stem cells, so that the "analytical methods used to study properties of the tumors are measuring properties which may be [those] of the majority of the tumor cell population (which may be responsible for [its] size, but not [its] growth) but not the properties of the stem line which is the minority responsible for the tumor growth." [Lajtha L. G., Stem Cell Concepts In: *Stem Cells, Their Identification and Characterization.* Ch. 1, pp 1-11 (Ed. C S Potten) Churchill Livingstone, London, 1983]. In terms of cell kinetics, it is important to distinguish between most of the divisions done by transit cells whose progeny will eventually be eliminated (hence the cell loss factors in tumors [Hall E. J. et al., Radiobiology for the radiologist 6th Edn p 359 Lippincott Williams & Wilkins, Philadelphia, Pa. 2006], and the much smaller number of divisions done by the precursor stem cells which maintain themselves and the supply of transit cells. Hence, kinetically, the stem cells determine treatment outcome. Yet most currently available treatments of cancers ignore this.

Since most cell survival of reproductive integrity assays (the most stringent endpoint) require that the cell be capable of undergoing only 5-6 divisions, as do transit cells in erythropoiesis (6-7 divisions), most such assays do not ask if the bulk of the proliferating (through only a few divisions) tumor cells (even the few tenths of a percent which grow in primary culture) are the tumor stem cells. Consideration of stem cells leads to the conclusion that: assays for tumor sensitivity to potential treatment agents should define clonogenicity as the ability to undergo 10 or more, rather than 5-6 divisions [Puck T. T. et al., *J Exp Med* 1956, 103: 653-666; Elkind M. M. et al., *The Radiobiology of Cultured Mammalian Cells*, pp. 69-74, Gordon and Breach, New York, 1967], so as to see the effect on the stem cells rather than on limited-future amplifying-division transit cells [Lajtha L. G., *Stem Cell Concepts* In: *Stem Cells, Their Identification and Characterization*. Ch. 1, pp 1-11 (Ed. C S Potten) Churchill Livingstone, London, 1983; Djordjevic B. et al., *Acta Oncologica* 2006, 45, 412-420].

Potential markers of human cancer stem cells have been reported, e.g., $CD44^+ CD24^{-/low} Lin^-$ as breast cancer markers [Al-Hajj M. et al., *Proc Natl Acad Sci USA* 2003, 100: 3983-3988]. However, the marker based detection of normal or cancer stem cells in the art can identify cells which are in most cases not stem cells. Much of the recent literature (1990-2008) regarding stem cells and in particular cancer stem cells (CSCs) has been based on antigenic markers used to identify the putative CSCs. The problem with this approach is that these markers do not identify such cells since: 1) the markers do not specify any function of the CSCs, they only help to enrich for subpopulations containing them; 2) cells possessing the appropriate markers (and lacking the inappropriate ones) are only enriched for CSCs and only a fraction of them can initiate a tumor; and 3) some cells lacking the appropriate markers supposedly defining CSCs are also able to initiate a tumor.

Thus, the prior art methods normally enrich, rather than identifying, cancer or normal stem cells. The previous methods, which employ monolayer and agar colony formation did not prevent stromal fibroblast outgrowth from producing artifactual colonies so that the cancer cell (not cancer stem cell) survival curves obtained by those methods were not useful or meaningless for predicting individual patient outcomes. In addition, the earlier methods (e.g., Djordjevic B. et al., *Radiat Environ Biophys* 1990, 29: 31-46; Lange C. S. et al., *Int J Radiat Oncol Biol Phys* 1992, 24(3): 511-518; Djordjevic B. et al., *Cancer Invest* 1991, 9(5): 505-512; Djordjevic B. et al., *Cancer Invest.* 1993, 1(3): 291-298; Djordjevic B. et al., *Acta Oncologica* 1998, 37: 735-739; Djordjevic B. et al., *Radiat Res* 1998, 150: 275-282) allowed the hybrid spheroids to attach to the culture vessel surface allowing a broad range of cancer cells (obscuring the behavior of the cancer stem cells) to spread out and produce colonies. Those early experiments did not use the more stringent 10 division end point. As such, amplifying transit cells of the tumor were dominant in the resulting sensitivity curves. This is clear from the 5-10% plating efficiency using the earlier method vs. the 0.5-0.76% plating efficiency with the nonattachment and the 10 division endpoint of the current patent application, i.e., ~90% of the colonies from the earlier methods were not cancer stem cells. Thus, there is a need for a method of measuring the proliferative ability of single cancer stem cells.

Although some mouse hematological tumors (leukemias and lymphomas) can be successfully transplanted into syngeneic hosts with one or a few tumor cell(s) [Hewitt H. B. et al., Nature 1959, 183: 1060-1061; Andrews J. R. et al, *Radiat Res* 1962, 16:76-81; Hill R. P. et al, *Brit J Radiol* 1973, 46: 167-174], the same is far from true for solid tumors [Djordjevic B. et al., Acta Oncologica 1998, 37: 735-739; Djordjevic B. et al., *Radiat Res* 1998, 150: 275-282; Djordjevic B. et al., *Indian J Exper Biol* 2004, 42: 443-447; Al-Hajj M. et al., *Proc Natl Acad Sci USA* 2003, 100: 3983-3988; Dick J. E., *Proc Natl Acad Sci USA* 2003, 100: 3547-3549; Kuperwasser C. et al., *Cancer Res* 2005, 65: 6130-6138; Jordan C. T. et al., *Curr Opinion Cell Biol* 2004, 16: 708-712.], even those selected by serial transplantation. For single-cell suspensions of solid tumors, the order of $10^4$-$10^6$ cells is usually required for the tumor to implant and grow [Elkind M. M. et al., *The Radiobiology of Cultured Mammalian Cells*, pp. 69-74. Gordon and Breach, New York, 1967]. For in vivo transplantation into syngeneic or immunologically compromised hosts, one could always argue that some minimal immunological response remained which sufficed to explain the large numbers of cells needed to ensure successful tumor implantation and growth. The $TD_{50}$ (tumor dose to yield 50% of hosts succumbing to the tumor) became the measure of the number of cells needed to produce a tumor, and the ratios of $TD_{50}$s for treated vs untreated tumor cells became the measure of the tumor cell surviving fractions and survival curves for each treatment modality [Hewitt H. B. et al., Nature 1959, 183: 1060-1061, Djordjevic B. et al., Acta Oncologica 1998, 37: 735-739; Djordjevic B. et al., *Radiat Res* 1998, 150: 275-282; Hall E. J. et al., Giaccia A J. Radiobiology for the radiologist 6th Edn p 359 Lippincott Williams & Wilkins, Philadelphia, Pa. 200].

An alternative explanation, particularly in the absence of an immunological response, is that only a small fraction of these cells are the cancer stem cells (CSCs) necessary for tumor engraftment and growth. Another factor which may come into play in the low rate of tumor initiation by marker selected CSCs is the need for a stem cell niche (micro-environment) suitable for maintenance of stemness [Schofield, R., *Blood Cells* 1978, 4: 7-25]. Injection of marker-selected cell populations into a mouse ignores the niche requirement, hoping that some CSCs will find one. Our hybrid spheroids (hs) appear to provide such a niche, enabling a fraction of the tumor cells comparable to that expected to be CSCs, to proliferate extensively (≥10 divisions). Presumably injection of such "growth defined hs into immunologically depressed (B and T cell null, NK cell low) xenograft hosts (NOD/SCID mice) may provide the necessary niche (for at least some of the CSCs in the hs) for tumor initiation.

In vivo models are not necessarily better than in vitro ones since "Transplantable tumors in small lab animals tend to be fast growing, undifferentiated, and highly antigenic and are grown as encapsulated tumors in muscle or underneath the skin, not in their sites of origin" [Hall E. J. et al., Giaccia A J. Radiobiology for the radiologist 6th Edn p 359 Lippincott Williams & Wilkins, Philadelphia, Pa. 2006]. Hence, much can be learned from in vitro studies too.

Nevertheless, the value of the confirming in vivo assay for solid tumors is that it tests for the ability of the nascent tumor to grow the necessary vasculature to permit more extensive tumor growth (to 1-2 cm diameter, equivalent to 37-40 divisions by a single CSC in the original hs).

The first attempt to measure the clonogenic survival of tumors in culture as an assay system was that of Salmon and Hamburger [Salmon S. E. et al., *Science* 1977, 197: 461-463]. Their system of tumor cell growth in soft agar produced sufficient cells to perform an assay in only about 25% of their patient samples and $10^5$ cells had to be plated to get a colony. The low plating efficiency ($PE=10^{-5}$) made it difficult to claim that the results were representative of the tumor in situ. Typical in vivo PEs of $10^{-6}$ in immunologically compromised hosts were no better. An improvement on these systems was based on the Courtney et al. double layer soft-agar method [Djordjevic, B. et al., *Cancer Invest* 1991, 9(5): 505-512,], used by West et al. [West C. M. L. et al., *Br J Cancer* 1997, 76: 1184-1190] to measure the sensitivity of cervical cancers to a single dose of 2 Gy. This method obtained results from about three quarters of patients and had a PE of about 0.1% ($10^{-3}$). A major benefit of the soft-agar methods was supposed to have been that they prevented the growth of stromal fibroblasts, which would otherwise take over the culture. However, Lawton [Lawton P. A. et al., *Radiother Oncol* 1994, 32(3): 218-225] and Stausbol-Gron et al. [Stausbol-Gron B. et al., *Radiother Oncol* 1995, 37(2): 87-99; Stausbol-Gron B. et al. *Radiother Oncol,* 1995, 37(2): 87-99; Stausbol-Gron B. et al. *Br J Cancer,* 1999, 79(7-8): 1074-84 and Schofield, R., Blood Cells 1978, 4: 7-25] showed that this assumption was incorrect; stromal fibroblasts also proliferate in agar, so that the results were for a mixture of fibroblasts and tumor cells, and not tumor cells only. Moreover, like all single-cell plating assays, there is a fundamental problem that soft-agar assays lack physiological relevance to in situ tumors, because they lack the three dimensional (3D) cell-cell contact seen in tumors, and the lack of a stem cell niche may be critical [Schofield, R., *Blood Cells* 1978, 4: 7-25; Stausbol-Gron B. et al., *Radiother Oncol* 1995, 37(2): 87-99; Stausbol-Gron B. et al. Radiother Oncol, 1995, 37(2): 87-99; Stausbol-Gron B. et al. Br J Cancer, 1999, 79(7-8): 1074-84]. This may be why no one has yet correctly predicted individual patient outcomes using these assays [West C. M. L. et al., *Br J Cancer* 1997, 76: 1184-1190; Hill R. P. *Cancer Res* 2006, 66: 1891-1895; Kern S. E. et al., *Cancer Res* 2007, 67; 8985-8988].

To alleviate these problems, an in vivo-like system, the hs assay has been developed [Djordjevic B. et al., Acta Oncologica 1998, 37: 735-739; Djordjevic B. et al., *Acta Oncologica,* 2006, 45, 412-420; Djordjevic B. et al., *Radial. Res.* 53rd Annual Meeting Program Book p 99 (PS179), Nov. 6-9, 2006, Philadelphia, Pa.; Hill R. P. et al., *Cancer Res* 2006, 66: 1891-1895; Kern S. E. et al., *Cancer Res* 2007, 67: 8985-8988; Djordjevic B. et al., *Radiat Environ Biophys* 1990, 29: 31-46; Lange C. S. et al., *Int J Radiat Oncol Biol Phys* 1992, 24(3): 511-518; Djordjevic B. et al., *Cancer Invest* 1991, 9(5): 505-512; Djordjevic B. et al., Cancer Invest. 1993, 11(3): 291-298], which is suitable for testing primary tumor cells (see below). This system exhibits a much higher PE, ~0.5-2% [Djordjevic B. et al., *Acta Oncologica,* 2006, 45: 412-420], with almost all samples producing sufficient colonies for assay [Djordjevic B. et al., *Acta Oncologica,* 2006, 45: 412-420; Djordjevic B. et al., *Radiat. Res.* 53rd Annual Meeting Program Book p 99 (PS179), Nov. 6-9, 2006, Philadelphia, Pa.; Hill R. P. et al., *Cancer Res* 2006, 66: 1891-1895]. This PE is consistent with the hypothesis that what formed colonies in vitro were the cancer stem cells (CSCs). Furthermore, in the hybrid spheroid system, cells are enveloped in a three-dimensional (3D) agglomerate of cells, initially providing an analog of the stem cell niche, and after treatment exhibiting all the mutual influences on survival. This is important, as it is becoming clear that the initial growth of CSCs depends on having an appropriate niche (plating of 40,000 single tumor cells fails to yield even one colony when ~400 would have been expected from the hs PE), and that the survival of tumor cells and the functionality of various tissues surrounding tumors are determined not only by the direct impact of inactivating agents, but also by the now well recognized Bystander Effect (BE) (see Choo A. et al., *J Biotechnol* 2006, 122: 130-141; Azzam E. I. et al., *Hum Exp Toxicol* 2004, 23: 61-65; Iyer R. et al., *Arch Biochem Biophys* 2000, 376: 14-25; Seymour C. B. et al., *Radiat Res* 2000, 153: 508-511; Ishii K. et al., *Int J Radiat Biol* 1996, 69: 291-299; Bishayee A. et al., *Radiat Res* 1999, 152: 88-97; Azzam E. I. et al., *Radiat Res* 1998, 150: 497-504; Djordjevic B., *BioEssays* 2000, 22: 286-290).

SUMMARY OF THE INVENTION

The present invention recognizes a functional assay based on the requirement that stem cells be capable of undergoing 10 or more divisions (i.e., 1.024-fold increase) by making hybrid spheroids, which are composed of fibroblasts and an average of about one cancer stem cell(s) per spheroid. According to the present invention, the cancer stem cells (CSCs) are recognized by their behavior (e.g., extensive growth). The fraction of tumor cells that are CSCs can be measured from their behavior, e.g., growth. The present invention recognizes that the spheroids provide a niche or microenvironment, which is suitable and necessary for the CSCs to grow and remain as CSCs. This niche is absent in monolayer and agar based assays that are used in the prior art assays for measuring cancer cells.

According to the present invention, the sensitivity of the CSCs to various treatments can be measured by the change in fraction of CSCs (based on the fraction of spheroids which grow), which grow after each treatment compared with that for untreated spheroids.

The present invention recognizes an assay for the sensitivity of individual patient's tumor's CSCs, the cells which will determine tumor recurrence or cure. The present invention also recognizes an assay for drug and other therapy testing to individualize patient treatments. The present invention further recognizes an assay for drug and other treatment development by testing their efficacy on a battery of individual patient tumor CSCs.

Accordingly, in one aspect, the present invention is directed to methods of measuring the proliferative ability of single cancer stem cells (CSCs).

According to the present invention, the method for measuring the proliferative ability of a single cancer stem cell contains the steps of obtaining a single cell suspension from a patient's tumor, engulfing the single cells in a spheroid of fibroblasts, preferably, engulfing an average of one cancer stem cell in a spheroid of fibroblasts and then detecting those spheroids in which a single cancer stem cell has grown at least 10 divisions. Assaying the patient's cancer stem cells' sensitivities to possible treatments is done by treating the newly formed spheroids with radiation, drugs, or other modalities and then measuring the decrease in the fraction of cancer stem cells which grow.

By the methods of the present invention it is now possible to treat individual cancer stem cells obtained from tumor cells engulfed in a spheroid of fibroblasts. Survivors amid those cancer stem cells have grown at least 10 divisions, while the surrounding fibroblasts have become reproductively dead and have disappeared. The cancer stem cells assayed by this methodology permit the tailoring of therapeutic modalities, such as chemotherapy, ionizing radiation and the like to remediate the patients condition on a selective basis, which is unique to each patient.

Accordingly, another aspect of the present invention is directed to a method for treating a cancer patient by providing an assay of the individual patient's tumor sensitivity, comprising measuring the proliferative ability of the cancer stem cells obtained from the patient. The present invention permits, for the first time, an ability to treat a patient with cancer as an individual rather than as an average of prior clinical experience by providing an assay of the individual patient's cancer stem cell sensitivity. The methods and assays contemplated herein permit the tailoring of patient treatment plans, taking into account the inherent sensitivities of the stem cells of their specific tumors.

In still another aspect, the present invention provides methods of detecting cancer stem cells from hybrid spheroids comprised of fibroblast cells, wherein said cancer stem cells proliferate through sufficient divisions, preferably, at least 10 divisions, while the surrounding fibroblast cells have become reproductively dead and have disappeared.

In yet another aspect, the present invention is directed to a method for drug development, wherein the effects of a drug or combination of drugs, and/or other proposed treatment modalities is determined on the individual patient's cancer stem cells.

In still yet another aspect, the present invention is directed to a method for providing a niche or appropriate microenvironment to permit CSC growth and maintenance of stem cell properties by engulfing tumor cells in a hybrid spheroid with fibroblasts which allows CSCs to grow.

In a further aspect, the present invention is directed to a method for validating or identifying candidate cell markers specialized for a cancer stem cell by obtaining appropriately marked tumor cells (e.g., by magnetic flow cytometry), engulfing the tumor cells in a hybrid spheroid at an average of about one such marked tumor cell per spheroid of fibroblasts, detecting the fraction of those marked cells which have grown at least 10 divisions.

DETAILED DESCRIPTION OF THE INVENTION

Figure 1:
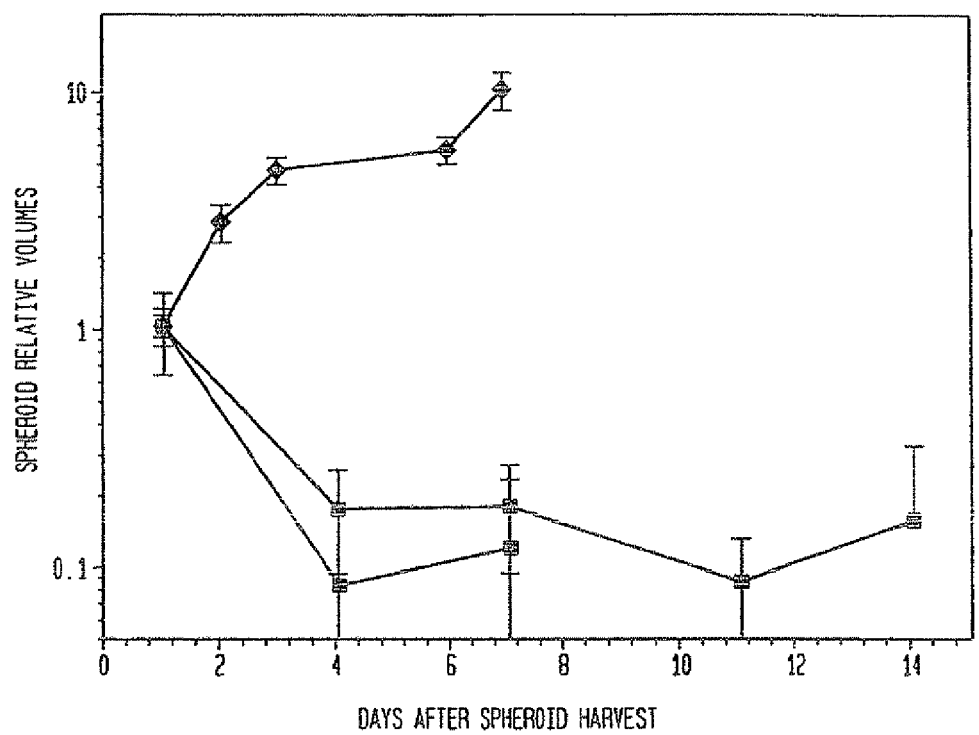
FIG. 1. Effects of time held in suspension on spheroid volume. Relative volumes of spheroids composed exclusively of live (darker squares), and supralethally irradiated (20 Gy, lighter squares) AG1522 fibroblasts are plotted for successive days after spheroid selection. Both types of spheroids shrank to about 10-20% of their original size within three days (day four after mixing the cells for spheroid creation), after which, they remain the same reduced size for the rest of the period of observation (up to two weeks). In contrast to the fibroblast results, pure spheroids of HeLa cells (diamonds) grow, increasing in size (volume) by an order of magnitude over a 6-day period. Data obtained from four experiments [Puck T. T. et al., *J Exp Med* 1956, 103: 653-66]. Error bars in this and in other graphs are standard errors of the mean.

The present invention recognizes a functional assay based on the requirement that stem cells be capable of undergoing 10 or more divisions (i.e., 1.024-fold increase) by making hybrid spheroids, which are composed of fibroblasts and an average of about one cancer stem cell(s) per spheroid. Ideally, each hybrid spheroid of the present invention contains a single cancer stem cell. Practically, the hybrid spheroids for use in connection with the methods of the present invention may contain zero, or a few, preferably, less than 10, more preferably, less than 5, most preferably, 1 cancer stem cell(s), with an average of about one cancer stem cell per spheroid. The present invention also recognizes using fibroblasts, preferably, unirradiated fibroblasts, as feeder cells in the hybrid spheroids. The present invention recognizes that the fibroblasts not only can prevent or inhibit cells, except cancer stem cells, from growing but also can shut down their own growth by themselves. For example, in a hybrid spheroid using fibroblasts as feeder cells, all fibroblasts, stromal fibroblasts, transient cancer cells, regular tumor cells and other specialized cells stop growing or die after a few divisions, e.g., 5 to 7 divisions. However, cancer stem cells continue to grow through at least 10 divisions. The present invention recognizes that another advantage of using fibroblasts as feeder cells is that there is also no need to irradiate the fibroblasts for use as feeder cells, thus avoiding or preventing artificial bystander effects.

Accordingly, one embodiment of the present invention is directed to methods of measuring the proliferative ability of single cancer stem cells. According to the present invention, the method for measuring the proliferative ability of a single cancer stem cell involves the steps of obtaining a single cell suspension from a patient's tumor, engulfing the tumor cells in a spheroid of fibroblast, preferably, engulfing an average of about one cancer stem cell in a spheroid of fibroblasts, then detecting those spheroids within which the cells have grown at least 10 divisions to show the presence of cancer stem cells, and assaying the single cancer stem cells.

The present invention utilizes a system of mixed aggregates of cells, to model in situ cell interactions to develop individualized treatment modalities for cancer patients. This three-dimensional (3D) system of floating cell aggregates, termed spheroids for their round shape, enables one to monitor their growth in both size and number of constituent clonogens and to measure survival curves for cells having 3D cell-cell interactions. This system was used to measure the three-dimensional cell-cell interactions on growth, and clonogenicity of either AG1522 fibroblasts, or HeLa cervical cancer cells (pure spheroids, or if both feeder and test cells are the same type, pseudohybrid spheroids), and/or of mixtures of both (hybrid spheroids). By following the increase or decrease in spheroid size, or number of clonogens per spheroid over time, one obtains growth or inhibition curves. By relating these clonogen numbers, one obtains, after a suitable growth period, relative survival. The system allows one to score the effects of irradiation and of other treatments, as well as the effect of interaction of the constituent cells on their survival. Floating pure, or pseudohybrid (composed of 10% live fibroblasts and 90% supralethally irradiated fibroblast feeder cells) spheroids, shrank to about 10-20% of their volume in two days and then remained at that size for at least fourteen days. In contrast, pure spheroids composed of live HeLa cells increased their volume by an order of magnitude over seven day period. Fibroblast clonogenicity decreases rapidly and exponentially over this time period, dropping to 1% in two days, <0.3% in three days and <1 per million within one week. Survival of cells in spheroids was measured by the ability of individual spheroids to grow beyond a size implying a thousand-fold increase of a single test (tumor) cell. A caveat to be observed is to correct survival for cellular multiplicity, i.e., reduce survival values to compensate for more than one colony former at the time of irradiation. The system of spheroids floating and growing in nutrient medium provides a selective system for evaluating growth of HeLa, and by implication, other neoplastic cells, without interference from (overgrowth by) normal fibroblasts. Thus it is possible to discriminate between normal and neoplastic cells by virtue of whether or not cells grow in spheroids in suspension. Such a system is useful for testing novel strategies (e.g., radiation in combination with chemicals), in an in vivo-like environment.

Cancer stem cells are the small fraction (~0.5-2%) of the tumor which has long-term growth potential and hence determines the success or failure of treatment; the bulk of the tumor consists of differentiating transit cells which are eventually eliminated (cell loss factor). Most assays study the 99% of the tumor which are irrelevant to treatment outcome. The hybrid spheroid 3D model discussed above is composed of a few cancer cells, but only one cancer stem cell, surrounded by feeder cells, is the only in vitro system which provides the niche for continued cancer stem cell growth and hence the possibility of their enumeration and measurement of their sensitivities to proposed treatment modalities. This can be done for each individual patient, thus avoiding ineffective therapies and allowing the optimal treatment to be given without delay.

This is the only model system, and a 3D one at that, which enables the measurement of the initial number and growth of cancer stem cells and tests their sensitivities to various proposed treatment modalities.

By "stem cell" is meant a cell having extensive proliferative capacity, e.g., 10 to 20 or more divisions, and capacity of self-renewal and differentiation. By "cancer stem cell" is meant a cancer cell in an original tumor that can self renew and regenerate the heterogeneous populations of self renewing and non-self renewing cancer cells present in the original tumor. A cancer stem cell can, but does not necessarily, arise from a normal stem cell.

By "hybrid spheroid" or "hs" is meant a three-dimensional (3D) system of mixed floating aggregates of cells. A hybrid spheroid enables one to monitor its growth in both size and number of constituent clonogens and to measure survival curves for cells having 3D cell-cell interactions. A preferred hybrid spheroid in accordance with the present invention is composed of one or more cancer cells, among which only one cancer cell is a cancer stem cell, surrounded by feeder cells, preferably, fibroblast feeder cells, more preferably, unirradiated fibroblast feeder cells.

In a particular embodiment, the method of the present invention can be automated. For example, spheroid volumes, as a function of time, will be estimated from their cross-sectional areas using either an automated counter, which may include, but not limited to, an inverted microscope with bright field and/or phase-contrast optics, automated stage and focusing, a high resolution cooled digital camera (1 μm resolution) and lens, a bar-code reader and a computer, or to obtain the preliminary data manually, e.g., by using a microscope without automation but with an eye-piece scale. From measured single cell volumes, the spheroid volumes will be converted into cell numbers. According to the present invention, growth of the spheroid is preferably conducted in an environment that can prevent attachment, spreading and or spheroid agglomeration, e.g., in Corning Ultra-Low Attachment (ULA) 96-well plates (or 384 or 1536 well ULA plates, when they become available). Final growth can also be measured by trypsinization of spheroids, followed by counting cells in the dispersed cell suspension. If a tumor stem cell was present, having undergone ≥10 divisions, a >1.000-fold increase, the remaining fibroblasts (reproductively dead) are <1% of the total cell number.

By the methods of the present invention it is now possible to treat individual cancer stem cells obtained from tumor cells engulfed in a spheroid of fibroblasts. Survivors amid those cancer stem cells have grown at least 10 divisions, while the surrounding fibroblasts have become reproductively dead and have mostly disappeared (i.e., <1% of the final cell number). The cancer stem cells assayed by this methodology permit the tailoring of therapeutic modalities, such as chemotherapy, ionizing radiation and the like to remediate the patient's condition on a selective basis, which is unique to each patient.

Another embodiment of the present invention is directed to a method for treating a cancer patient by providing an assay of the individual patient's tumor sensitivity, comprising measuring the proliferative ability of the cancer stem cells obtained from the patient. The present invention permits, for the first time, an ability to treat a patient with cancer as an individual rather than as an average of prior clinical experience by providing an assay of the individual patient's tumor's CSC sensitivity. The methods and assays contemplated herein permit the tailoring of patient treatment plans, taking into account the inherent sensitivities of their specific tumors and their CSCs.

In still another embodiment, the present invention provides methods of detecting cancer stem cells in hybrid spheroids comprised of fibroblast cells, wherein said cancer stem cells proliferate through sufficient divisions, preferably, greater than 10 divisions, while the surrounding fibroblast cells have become reproductively dead and have disappeared.

In yet another embodiment, the present invention is directed to a method for drug development, wherein the effects of a drug or combination of drugs or other treatment modalities is determined on the individual patient's cancer stem cells.

The assay contemplated by the present invention can be used for drug development whereby the effects of a drug or combination of drugs can be determined on the cancer stem cells rather than on the other 99% of tumor cells which are not responsible for tumor recurrence.

In still yet another embodiment, the present invention is directed to a method for providing a niche or appropriate microenvironment to permit CSC growth and maintenance of stem cell properties by obtaining tumor cells, engulfing the tumor cells in a hybrid spheroid with fibroblasts and detecting the presence of CSCs by their growth.

In a further embodiment, the present invention is directed to a method for validating or identifying candidate cell markers specialized for a cancer stem cell by obtaining appropriately marked tumor cells (e.g., by magnetic flow cytometry), engulfing the tumor cells in a hybrid spheroid at an average of about one such marked tumor cell per spheroid of fibroblasts, detecting the fraction of those marked cells which have grown at least 10 divisions. This method can also be used for validating previously proposed cancer stem cell markers.

The present invention also provides the following non-limiting examples.

EXAMPLE 1

Research Methods

Types of Spheroids:

Two types of spheroids are used in this study: (1) Pure fibroblast spheroids, in which all the cells are fibroblasts; (2) Hybrid spheroids, in which two cell types are mixed (primary breast cancers, mixed with fibroblasts), one type being the test cells whose growth and viability are being measured (0.5% to 40% of the initial spheroid cells), while the other type consists of nonclonogenic fibroblast feeder cells (99.5% to 60% of the initial spheroid cells; rendered such by culture condition).

Cell Lines Used:

Two cell types can be used: human diploid fibroblasts (either AG1522 early passage male or RMF-EG hTERT immortalized GFP labeled female) retrieved from liquid nitrogen storage shortly before use, and cells obtained directly from breast cancer surgical samples.

Tumors to be Studied:

Tumors tissues are obtained from patients to be analyzed. For the examples provided below, Dr. Schwartzman, Chief of General Surgery in the Surgery department of Downstate Medical Center, State University of New York, provides a supply of breast tumors. All clinical material will be available under IRB Study 406-073 "Testing of tumor cell sensitivity to radiation and chemotherapeutic agents using hybrid spheroids", approved as Exempt.

Obtaining a Single Cell Suspension of Tumor Cells:

The tumor sample, under aseptic conditions, is washed (3×) in phosphate-buffered saline (PBS), placed in a Petri dish and cut with crossed scalpels into ~2 mm cubes. The cubes are forced through a stainless steel wire mesh (2 mm squares) to provide a brei of cells which are then placed in a spinner flask in a solution of Collagenase and DNase (20 mL of MEM supplemented with 20 mM HEPES, 47.5 mg Collagenase D, 312.5 ng DNAse). The suspension is kept in a spinner flask at 37° C. overnight. The next day, the cells are centrifuged into a pellet, resuspended in fresh medium (MEM supplemented with 10% fetal bovine serum (FBS), and antibiotics) and an aliquot counted on a hemacytometer. An appropriate amount is mixed with a suspension of fibroblasts (in the same medium) to make spheroids, as described below.

Spheroid Formation and Maintenance:

The method of spheroid formation has been described previously [Djordjevic B. et al., *Radiat Environ Biophys* 1990, 29: 31-46; Lange C. S. et al., *Int J Radiat Oncol Biol Phys* 1992, 24(3): 511-518; Djordjevic, B. et al., *Cancer Invest* 1991, 9(5): 505-512; Djordjevic B. et al., Cancer Invest. 1993, 11(3): 291-298; Djordjevic B. et al., *Acta Oncologica* 1998, 37: 735-739]. Briefly, a mixed cell suspension composed of cells to be tested (tumor cells) and fibroblasts is co-incubated overnight, in an ultra-low attachment (or non-wettable surface bacteriological) Petri dish, to which cells do not adhere. Under these conditions, hs are formed, the composition of which closely corresponds to the input of the original cell mixture [Djordjevic B. et al., *Radiat. Res. 53rd Annual Meeting Program Book* p 99 (PS179), Nov. 6-9, 2006, Philadelphia, Pa.; Djordjevic B. et al., *Radiat Environ Biophys* 1990, 29: 31-46; Lange C. S. et al., *Int J Radiat Oncol Biol Phys* 1992, 24(3): 511-518; Djordjevic, B. et al., *Cancer Invest* 1991, 9(5): 505-512; Djordjevic B. et al., Cancer Invest. 1993, 11(3): 291-298; Djordjevic B. et al., Acta Oncologica 1998, 37: 735-739; Djordjevic B. et al., *Indian J Exper Biol* 2004, 42: 443-447]. After formation, hs of desired sizes are selected, by passing the entire harvest of cell agglomerates through a sterile system of nylon sieves, and then eluted from selected sieves. Most of the hs passing a 125 μm, and arrested on a 88 μm pore sieve are 100-110 μm in diameter, containing about 170 cells. For higher radiation (or chemotherapy) doses, other size hs containing 134 cells (88-105 μm), 340 cells (105-125 μm), etc., up to 2,280 cells (~250 μm), are used. A mixture of $3-5 \times 10^6$ AG1522 fibroblasts and ~5.5% that of tumor cells yields 88-105 μm and 105-125 μm diameter hs with an average of about 0.7 and 2.6 tumor cell clonogen(s) per spheroid, respectively (see above cervical cancer PEs). Multiplicity and surviving fractions of clonogenic tumor cells are readily measured (with only one clonogenic test cell in a spheroid, there will be no growth if that cell is sterilized or there will be growth if it survives; as demonstrated in [Djordjevic B. et al., *Radiat Environ Biophys* 1990, 29: 31-46; Lange C. S. et al., Int J Radiat Oncol Biol Phys 1992, 24(3): 511-518; Djordjevic, B. et al., *Cancer Invest* 1991, 9(5): 505-512; Djordjevic B. et al., Cancer Invest. 1993, 11(3): 291-298; Djordjevic B. et al., Acta Oncologica 1998, 37: 735-739]). RMF-EG (female) fibroblasts (which can be distinguished from tumor cells by their GFP fluorescence) will be used as an alternative to AG1522 cells, in experiments to confirm that what has grown is not fibroblasts. For the former cells, DMEM is used instead of MEM. Spheroids made exclusively of fibroblasts (pure spheroids), are used as tumor-free controls. In addition to clearly discernable morphological differences between breast tumor cells and fibroblasts, the AG1522 fibroblasts are distinguishable as male cells (Y chromosome painting using fluorescent in situ hybridization (FISH), in fixed cells) and the RMF-EG fibroblasts contain green fluorescent protein (GFP) making them distinguishable in live cell preparations under fluorescence microscopy or flow cytometry (with the possibility of sorting). The GFP also distinguishes the RMF-EG feeder cells from tumor sample stromal fibroblasts (and their descendants, if any). Aliquots of the spheroids are counted and diluted in medium, so that 0.1 mL in each well of a series of 96-well Corning ultra low attachment plates yields an average of 1 spheroid/well. The number of spheroids/well follows a Poisson distribution [Djordjevic B. et al., *Acta Oncologica*, 2006, 45, 412-420], as does the number of test cells/spheroid [Djordjevic B. et al., *Radiat. Res. 53rd Annual Meeting Program Book* p 99 (PS179), Nov. 6-9, 2006, Philadelphia, Pa.].

Principal Features of the hs Assay:

The principal feature of our hs assay, as used in [Djordjevic B. et al., *Acta Oncologica*, 2006, 45, 412-420; Djordjevic B. et al., *Radiat. Res. 53rd Annual Meeting Program Book* p 99 (PS179), Nov. 6-9, 2006, Philadelphia, Pa.; and Djordjevic B. et al., *Radiat Res* 1998, 150:275-282; Djordjevic B. et al., *Indian J Exper Biol* 2004, 42: 443-447] and for the proposed study, is to monitor the capacity of spheroids to grow beyond a size equivalent to 10 divisions by the tumor cells plus the reduced remainder of the fibroblasts; this is assumed to denote the ability of unlimited test cell proliferation. The hs assay also prevents fibroblasts (potentially emanating from surgical specimens) from growing and being scored in survival experiments. To obtain growth of neoplastic cells, hs are incubated in Corning Ultra Low Attachment 96-well plates, (17-27 days), in which there is no cell attachment. Under such conditions, unirradiated fibroblasts fail to grow in floating spheroids; they are easily distinguished from tumor cells on the basis of morphology (or Y chromosome staining or GFP) upon dispersal and replating. This enabled us to measure the Plating Efficiency (PE) of primary cervical carcinoma cells and to monitor the radiation response of test HeLa cells, whereby growth beyond a certain size signifies survival, in a manner analogous to colony formation (but with much higher stringency, since the latter requires only 5-6 divisions). Using an earlier system of hs with supralethally irradiated HeLa feeder cells, we obtained clonogen survival curves for a wide variety of tumors (including breast), either irradiated or treated with chemotherapeutic agents [Djordjevic B. et al., *Radiat Environ Biophys* 1990, 29: 31-46; Lange C. S. et al., Int J Radiat Oncol Biol Phys 1992, 24(3): 511-518; Djordjevic, B. et al., *Cancer Invest* 1991, 9(5): 505-512; Djordjevic B. et al., Cancer Invest. 1993, 11(3): 291-298; Djordjevic B. et al., *Acta Oncologica* 1998, 37: 735-739].

Automation of the Spheroid Volume Measurements:

At present, the limitation on the number of tumors and conditions that can be studied (with at least 3 replicate plates each), has been the labor intensiveness of the spheroid diameter (and volume) measurements. With an automated system for spheroid volume and growth curve measurements with resolution of ~1 µm, and database storage of the original data images as well as computed results, the process can be automated. Plates will be identified by bar codes for tracking repeated plate readings over time. Wells are defined by row and column. Each well will be scored for number of spheroids, their positions and areas, from which each spheroid volume will be estimated. This will enable the processing of ~75-100 plates a day (per such automated microscope) and make all of our proposed growth and survival curve measurements feasible at a reasonable per assay cost. For the radio-chemo-sensitivity assays, with 5 radiation doses and 3 drugs with 4 doses each (with 2 spheroid sizes, 3 replicates per condition), 2 tumors can be processed simultaneously, totaling 33 tumors/year. Using only 2 doses (control and 1 dose) for each treatment (as most other assays do to estimate sensitive or resistant), ~5 tumors can be processed at a time, or ~83 tumors/year per such automated microscope. These numbers are based on 96-well plates; use of 384- or 1536-well plates will increase the numbers by 4 or 16 fold, respectively.

Dispersal of Spheroids for Cellular Content Studies:

To determine the number of cells per spheroid, either in order to follow the growth pattern of spheroids, or for the purpose of measuring cellular multiplicity (see below), a known number of spheroids are trypsinized. After dispersal, the cells are counted and a second round of hybrid spheroid formation and growth can be measured. From these data (cell numbers, colonies formed per spheroid) one obtains the growth of spheroids as a function of time and the average clonogen number per spheroid; at the time of irradiation the latter is the cellular multiplicity (M). Tumor cells grown in hs, when trypsinized and plated are easily distinguished morphologically from AG1522 and RMF-GP cells.

X-irradiation (or chemotherapeutic agent treatment (e.g., Lange C. S. et al., Int J Radiat Oncol Biol Phys 1992, 24(3): 511-518; Djordjevic, B. et al., *Cancer Invest* 1991, 9(5): 505-512; Djordjevic B. et al., Cancer Invest. 1993, 11(3): 291-298; Djordjevic B. et al., Acta Oncologica 1998, 37: 735-739) and measurement of survival of spheroids: For irradiation studies (see Djordjevic B. et al., *Radiat. Res. 53rd Annual Meeting Program Book* p 99 (PS179), Nov. 6-9, 2006, Philadelphia, Pa.; Djordjevic B. et al., *Radiat Environ Biophys* 1990, 29: 31-46; Lange C. S. et al., Int J Radiat Oncol Biol Phys 1992, 24(3): 511-518; and Djordjevic B. et al., *Radiat Res* 1998, 150:275-282; Djordjevic B. et al., *Indian J Exper Biol* 2004, 42: 443-447), spheroids eluted from the selected sieve are counted and distributed, with an average of one spheroid per well of a series of 96-well ultra low attachment plates (≥3/dose), and irradiated with 0-8 Gy doses of 250 kVp X-rays from a Philips RT 250 therapy machine (15 mA, 2 mm Al inherent filtration, HVL 0.475 mm Cu, 50 cm FSD, dose rate 2.7 Gy/min). At the end of the incubation period allowed for scorable spheroid formation (10-21 days, depending on growth rate), spheroids over 156 µm in diameter (volume >2×10$^6$ µm$^3$) are counted (for HeLa cells with a 20 µm diameter; other sizes for smaller cells, corresponding to the same cell number increase). These spheroids, now composed chiefly of tumor cells, reflect growth from one or a few clonogens to a spheroid containing about 1,038 to 2,075 cells, so the tumor cells in hs must have undergone ~10-11 doublings (divisions) per original clonogen. Spheroid Survival is determined by relating the number of such enlarged spheroids in the treated plates, to that in the control plates [Djordjevic B. et al., *Acta Oncologica*, 2006, 45, 412-420; Djordjevic B. et al., *Radiat. Res. 53rd Annual Meeting Program Book* p 99 (PS179), Nov. 6-9, 2006, Philadelphia, Pa.; and Djordjevic B. et al., *Radiat Environ Biophys* 1990, 29: 31-46; Lange C. S. et al., Int J Radiat Oncol Biol Phys 1992, 24(3): 511-518; Djordjevic, B. et al., *Cancer Invest* 1991, 9(5): 505-512; Djordjevic B. et al., Cancer Invest. 1993, 11(3): 291-298; Djordjevic B. et al., Acta Oncologica 1998, 37: 735-739; Djordjevic B. et al., *Radiat Res* 1998, 150:275-282; Djordjevic B. et al., *Indian J Exper Biol* 2004, 42: 443-447]. It is important to note that these spheroids, having diameters <200 µm, are fully aerobic, are too small to have hypoxic centers, and at the time of irradiation or other treatment, are even smaller.

Cellular Multiplicity Corrections of Spheroid Survival:

To obtain single cell survival curves, fractional survival of whole spheroids is corrected for cellular multiplicity [Puck T. T. et al., *J Exp Med* 1956, 103: 653-666; Sinclair W. K. et al. *Nature* 1964, 203: 247-250] using the equation:

$$SF_{(s.c.)} = 1 - (1 - SF_{(spher)})^{1/M}$$

[Sinclair W. K. et al. *Nature* 1964, 203: 247-250]

where $SF_{(s.c.)}$ is the surviving fraction of single clonogens, $SF_{(spher)}$ is the surviving fraction of whole spheroids, and M is the average multiplicity of test cells in the control (unirradiated) series at the beginning of the irradiation procedure. M will be obtained in two ways. By limiting dilution of tumor cells in spheroids, such that the number of clonogenic tumor cells/spheroid is <<1, the fraction of unirradiated spheroids which grow (contain ≥1 clonogen or CSC) provides the multiplicity of clonogens/spheroid. Alternatively, by using two different size spheroids from the same preparation, the shift of their parallel survival curves, corrected for their tumor cell contents, yields the single cell extrapolation number and hence, M [Djordjevic B. et al., *Indian J Exper Biol* 2004, 42: 443-447]. It should be noted that multiplicity denotes the clonogen content per spheroid at the time of irradiation, and not at the time of spheroid scoring at the end of the incubation period for spheroid survival determination.

Spheroid Growth Measurements:

Spheroid volumes, as a function of time, will be estimated from their cross-sectional areas using the automated counter (an inverted microscope with eye-piece scale was used to obtain the preliminary data). From measured single cell volumes, the spheroid volumes will be converted into cell numbers. Growth in Corning Ultra-Low Attachment 96-well plates prevents attachment and spreading. The wells also prevent spheroid agglomeration. Final growth can also be measured by trypsinization of spheroids, followed by counting cells in the dispersed cell suspension. If a tumor stem cell was present, having undergone ≥10 divisions, a >1.000-fold increase, the remaining fibroblasts (reproductively dead) are <1% of the total cell number.

In Vivo Measurements to Test for CSCs:

Putative hsCSC-containing hs will be injected subcutaneously above the right scapula and the left hip of NOD/SCID mice (B and T cell null, NK cell low) which readily accept xenografts. The contra-lateral sites will receive either pure fibroblast spheroids as controls or low growth (presumably no CSCs) spheroids to test for the absence of CSCs in such spheroids. The lymphatic drainage is such that each site is isolated from the others [Biology of the Laboratory Mouse, First Edition (1941, ed. G D Snell) p 293; Second Edition (1966, ed. EL Green) pp 251-253. The Jackson Laboratory, Bar Harbor, Me.]. Size of the implants will be measured 3 times/week (for 6-8 weeks) using sterile stainless steel Castroviejo calipers and the sizes measured from the calipers using a Fowler NSK MAXCAL digital caliper with 10 μm resolution. Growth will be followed until it is clear that there is either no growth or the tumor disappears (expected for those spheroids not containing hsCSCs) or conversely, the tumor grows to a diameter of 1-2 cm. When this size has been attained, the animal will be sacrificed for histology of the growth(s). Excised tumors will be weighed and then fixed in formol saline embedded in paraffin, serial sectioned and alternate slides stained with H&E. The H&E stained slides will be used to examine for the presence of neovascularization of the growing tumor. Intermediate slides will be kept for staining with putative stem cell markers (IHC, immunohistochemistry). From each mouse where tumor growth was observed, an aliquot of the tumor will be harvested into tubes to be subsequently analyzed to determine human/mice origin of the cells. The mice will be maintained and all procedures will be done aseptically (in a laminar flow hood) to protect the health and viability of these specific-pathogen-free mice. These animal experiments were approved by the SUNY Downstate Medical Center IACUC entitled: Evidence for Cancer Stem Cells in Hybrid Spheroids Grown from Human Cancers.

Cancer Stem Cells and their Markers:

The presence and frequency of the reported human breast (or other solid tumor) stem and tumor cell markers (see below) are tested on selected clonal populations of tumor functional stem cells derived from growth (>10 divisions) in hybrid spheroids. Conversely, these markers will also be used to select putative cancer stem cells from fresh tumor single cell suspensions for testing in hybrid spheroids for the increase in >10 division clones corresponding to tumor stemness. This will help elucidate potential relationships among tumor stem cells and normal tissue stem and progenitor cells. For example, these results could demonstrate the likelihood that breast tumor stem cells result from pluri- (or toti-) potent stem cells, rather than by the acquisition of mutations for stem-like behavior by the more differentiated cells of the breast. Dick (Dick J E. *Proc Natl Acad Sci USA* 2003; 100: 3547-3549) suggests that solid tumors may also follow the paradigm of the important role of a niche for the tumor stem cells. By demonstrating functional cancer stem cells in hybrid spheroids suggests that surrounding fibroblasts (in 3D) may fill that role (see above). As such, comparing marker expressions between tumor cells before and after passage through hybrid spheroids and selection of cells from high and low proliferative spheroids can provide a means of studying the niche requirements for the maintenance of stemness and for validation CSC and tumor cell markers.

Stem and Tumor Cell Marker Methods:

Spheroid-derived breast tumor stem cells and alternatively, non-stem cells, will be assessed for the presence of breast stem and/or tumor cell markers by (a) immunofluorescence microscopy (IFM) and (b) flow cytometry (FCM). Spheroids will be collected, pooled (by size group) and dispersed by trypsinization as described above which will provide a yield of at least ~1-5×10$^4$ cells per well.

Antibodies to be used for breast tumors (for flow cytometry and magnetic bead separations) are: anti-CD44 (allophycocyanin (APC), phycoerythrin (PE) or biotin)(Invitrogen/Dynal, Brown Deer, Wis.), anti-CD24 (PE or FITC)(Biolegend), anti-B38.1 (APC), anti-epithelial-specific antigen (ESA)-FITC (Biomedia, Foster City, Calif.). Lineage markers will be anti-CD2, -CD3, -CD16, -CD18, -CD31, -CD64 (all Invitrogen), -CD10 and -CD140b (Pharmingen for FCM, (streptavidin-linked from PerSeptive Diagnostics, Cambridge, Mass. for magnetic bead separations)). Antibodies are directly conjugated to various fluorochromes or magnetic beads, depending on the experiment, as described in [21,14]. The Lin-cells will be negatively selected using magnetic beads to bind all of the above listed Lineage markers.

IFM:

Cells will be collected, allowed to attach in 96-well tissue culture (TC) surface plates, then fixed to the plates with 4% paraformaldehyde for 10-30 min Cells will be washed in PBS and incubated with appropriately diluted fluorophore (FITC, PE, etc.) conjugated anti-cell-surface (CD) antibody in PBS/ 0.1% BSA overnight at 4° C. as previously described [Bluth M. H. et al., FASEB Journal 2006, 20:A1106]. Alternatively, cells will be incubated with primary (unconjugated) anti-cell surface marker antibodies overnight at 4° C., subsequently washed in PBS and incubated with appropriately species matched fluorophore conjugated anti-primary antibody for 1 hr at room temperature (RT). Fluorescence will be determined by visualizing cells under an inverted fluorescence microscope (Olympus) with appropriately filtered wavelengths. The presence and number of fluorescent cells per cellular field will be counted.

Flow Cytometry:

Trypsin (or collagenase) dispersed spheroids will be washed in PBS and incubated with fluorophore (FITC, PE, etc.) conjugated anti-tumor and/or stem cell marker antibodies, as described above, for 10 min at room temperature (RT). Alternatively, cells are incubated with primary (unconjugated) anti-cell surface marker antibody for 30 min at RT, subsequently washed 3× in PBS and incubated with appropriately matched fluorophore conjugated anti-primary antibody for 10 min at RT. After removal of Lin+ cells using magnetic beads (see below), the remaining markers are scored with Flow Cytometry. The analysis is performed on either a Coulter Epics XL/MCL Flow Cytometer using System II software (Coulter) and CytoComp (Coulter) [Bluth M. H. et al., FASEB Journal 2006, 20:A1106; Bluth M. H. et al., Clin Immunol 2003, 108:152; Bluth M. H. et al., *Human Immunology* 2005; 66:1029-1038] or BD Biosciences FACS AIRA 13-color flow cytometer. Forward and side scatter are used to identify the spheroid-derived cell populations and characteristic cell type markers, where available, are used to establish optimal gates as described previously [Bluth M. H. et al., FASEB Journal 2006, 20:A1106; Bluth M. H. et al., Clin Immunol 2003, 108:152; Bluth M. H. et al., *Human Immunology* 2005; 66:1029-1038]. A minimum of 5,000 events are collected. The gain on the photomultiplier tube detecting fluorescence intensity is adjusted so that 99% of cells with background fluorescence staining are scored between $10^0$ and $10^1$ on a 4-decade log scale. Specific fluorescence is reported as the percentage of cells with relative fluorescence intensity scored above background. Control values are then subtracted from experimental values. Data will be expressed as % of population.

Magnetic Bead Separations of Cells with Tumor and/or Stem Cell Markers:

Cells will be separated using the OptiCell Magnetic separation system, which uses paramagnetic Dynabeads to select cells bearing markers which attach to the antibody-coated magnetic beads, (Dynal, Lake Success, N.Y.) using an MPC-1 magnet (Dynal), and detatched using DetachaBeads (Dynal), according to manufacturer's recommendation. Selection is either positive by binding and subsequently releasing cells bearing the desired marker(s) (e.g., CD44, CD24 or ESA), or negative by binding and removing cells with markers to be excluded (e.g., Lineage markers). Where feasible, the reverse procedure will also be performed so that the desired cells will have been negatively selected and therefore not at risk that the selection/release process might have altered them. Briefly, tumor/stem cell surface specific antibodies will be linked to beads (i.e., biotin linked antibody, streptavidin linked microbead system—Miltenyi Biotec or Dynal) as described by manufacturer. Beads will be prewashed in Dynal washing buffer (i.e., bead to target cell ratio for binding at 4:1). The incubation for binding of beads to cells is performed for 10 min at 4° C. with gentle rocking (or mix by hand once every minute). After binding, the final volume is brought to 10 ml with cold washing buffer. Cell/bead suspension will be injected into the OptiCell with a 10 cc syringe, with air bubbles removed. The OptiCell will be gently shaken to disperse the cell/bead suspension. The device's magnet will be applied firmly to one side of the OptiCell, which will be incubated horizontally at 4° C. for 2 min with the magnet attached to the bottom surface of the OptiCell. Eight ml of air will be slowly injected, the OptiCell rotated 2 times and buffer and unbound material will be removed and discarded. Ten ml fresh cold washing buffer will be added to the OptiCell, air bubbles removed and the suspension will be incubated horizontally for 1 min at 4° C. with the magnet attached to the bottom surface. These incubation/wash steps will be repeated twice more, after which the magnet will be detached from the OptiCell. Ten ml of culture medium will be added to the OptiCell with a 10 cc syringe, air bubbles removed and the reaction chamber will be gently shaken to disperse the cells. Positively selected cells will be examined by IFM or flow cytometry and cultured and/or analyzed as needed. In addition, nucleic acid-based bead separation for select genes, as may be needed, will be employed as per manufacturer's recommendation (Dynal). A recent *Nature* paper [Hatfield S. D. et al., *Nature* 2005, 435(4044): 974-978] shows that *Drosophila* germ line stem cell division is regulated by microRNAs, so this examination may be revealing.

Statistical Methods:

Data will be presented as means with standard errors of the results of multiple plates/dishes, normalized to unity (for survival curves) within each experiment, prior to combining the data of replicate experiments. The standard errors of ratios (as in plating efficiencies and surviving fractions) are determined using the chain rule for equipartition of variance, which takes into account the proper weight of the uncertainty contributions of both the numerator and the denominator, as well as, for more complex relationships, the mathematical function describing the relationship between the measured parameters [Hald A., *Statistical Theory with Engineering Applications*. John Wiley & Sons, Inc., New York, 1952. See sections 5.7-5.9 and 5.16-5.17, esp. Eq. 5.17.7; Lange C. S. et al., *Biopolymers* 1977, 16: 1063-1081].

Disease Impact:

Current treatment of breast cancer, and indeed most solid tumors, is based on clinical trials which compare the safety and efficacy of a proposed new treatment with that of the current standard-of-care. However, the selection of new treatment modalities depends on laboratory tests which make two questionable assumptions: 1) that the tumor cells which must be sterilized are represented by the bulk of the tumor; 2) that tumors of a given stage and grade in different patients will have the same response. If the cancer stem cell hypothesis (for which considerable evidence has accumulated (see Background), is correct, the first assumption is wrong. If some patients have more sensitive tumor than do others, and inter-patient tumor heterogeneity is well documented, then the second assumption is wrong. Both assumptions impact what agents are chosen for clinical trials. Agents that do not kill (sterilize) most of the tumor cells are dropped from further consideration. Yet these agents may well be the ones which are effective against the surviving cancer stem cells which are responsible for recurrence. What works well for one patient may not be effective for another. This is seen clearly with stage I-III cervical cancer patients, where in a protocol used at the Christie Hospital, Manchester, England, patients were given radiotherapy followed by hysterectomy, yet measurements of individual patient tumor radiosensitivity (using the Courtney-Mills double layer agar colony method for surviving fraction after 2 Gy (SF2)) indicated that if one could recognize which patients had the more sensitive tumors, they could be spared the hysterectomy. Tumor radiosensitivity (SF2) was a strong and "significant prognostic factor for overall survival, local control, and metastasis-free survival." The 5-year survival rate was 81% for those with SF2 below the median, versus 51% for those with SF2 above the median. SF2 was "independent of disease stage, tumor grade, patient age, colony-forming efficiency and tumor diameter. In a multivariate analysis, radiosensitivity was the most important variable and, after allowing for this, only stage was a significant predictor of treatment outcome." Unfortunately, the poor precision of the agar assay for the individual patient prevented its use for treatment planning [West C. M. L. et al., *Br J Cancer* 1997, 76: 1184-1190]. Interestingly, this result was despite the fact that similar studies with head and neck tumors showed that: 1) fibroblasts grow in agar, 2) 2-33% of colonies contained tumor cells (Cytokeratin AE-1-3 positive) while 83-100% of the colonies were 5B5 fibroblast antibody positive, and 3) the overall SF2 was highly correlated to the fibroblast SF2 [Lawton P. A. et al., *Radiother Oncol* 1994, 32(3): 218-225; Stausbol-Gron B. et al., *Radiother Oncol* 1995, 37(2): 87-99]. Further studies (71 patients) showed that overall median PE was 0.052% (an order of magnitude lower than our hs assay result for putative cervical cancer stem cells), the majority of colonies contained fibroblasts while the proportion with tumor marker ranged from 1 to 88% with a median of 15% [Stausbol-Gron B. et al. Radiother Oncol, 1995, 37(2): 87-99; Stausbol-Gron B. et al. Br J Cancer, 1999, 79(7-8): 1074-84]. The overall SF2 correlated with the fibroblast SF2 but not the tumor SF2 and tumor cell and fibroblast radiosensitivities for the same individual were not correlated. Hence there is a real need for an assay which measures the tumor cells' (and most likely the tumor stem cells) radiosensitivity without the fibroblast-induced confounding (absent in the hs assay). An assay which tests the sensitivity of those tumor cells responsible for determining cure, and doing so for each individual patient (correcting for inter-patient heterogeneity), would have a major impact on cancer cure rates because each patient could then be treated with only those agents which are most effective for their particular cancer. This would enable one to tailor the combination of treatment agents to use only those most effective against the cancer's stem cells while avoiding those which are less effective or not effective. Activity against the bulk of the tumor may cause rapid shrinkage, but if the underlying cancer stem cells survive, recurrence will follow. Since most treatments are limited by the dose-limiting normal tissue tolerance, avoiding the use of agents ineffective for that patient's tumor would increase cure rates by allowing other agents to be used instead, while still remaining within the normal tissue tolerance total effective dosages. Consideration of cancer stem cells (CSCs), and an assay to measure their sensitivity for each patient's cancer, suggests that these two problems can be solved and cure rates considerably enhanced. The hybrid spheroid (hs) of the present invention system represents a powerful tool to study and elucidate tumor cell ontogeny. It also provides a mechanism for screening the effect of anti-tumor therapy (radiation, chemo-therapy, biologics, etc.) on a cellular level, thereby providing a platform for potential individualized patient treatment. We have already shown that this assay (even in its earlier versions with supralethally irradiated HeLa feeder cells and thus subject to a Bystander Effect) can provide single cell clonogenicity survival curves for both ionizing radiations (the only assay to do so) and chemotherapeutic agents. Most other assays fail to provide meaningful radiation survival curves because they use neither a clonogenicity endpoint, nor such a stringent definition of clonogenicity. The present invention can show: 1) if the clonogenic cells in hs are CSCs, using both in vitro and in vivo measurements, under conditions where an analog of the stem cell niche is provided (the hs), 2) provide survival curves for individual patient tumors to determine the range and distribution of inter-patient heterogeneity of radio- and chemo-sensitivity (under conditions which mimic the in vivo Bystander Effect situation), and 3) provide initial estimates of the correlation between such sensitivities and treatment outcome. If tumor cure or treatment failure are indeed determined by the sensitivity of the cancer stem cells rather than the limited proliferative capacity cells comprising the bulk of the tumor, then the hybrid spheroid assay could provide a useful method for individualizing patient treatment. "In developing new cancer therapeutics, analyses that directly assess toxicity towards tumor stem cells are an important priority"[Bonnet D. et al., Nat Med 1997, 3: 730-737].

The present invention recognizes methods to study CSCs themselves. Kinetically, the stem cells determine treatment outcome, so the hybrid spheroid assay in accordance with the present invention for cancer stem cell (CSC) response to potential treatment modalities and components provides the possibility of tailoring the treatment plan to each individual patient based on the sensitivities of their CSCs. This approach has never been done in the art.

The impact could be dramatically increased cancer cure rates since each component of a treatment plan would have been selected for its effectiveness (singly and in combination) against the cells which matter in that patient. The data we propose to collect from ~100 patients will give us an estimate of the inter-patient variability in breast cancer stem cell response to the individual and combined components of standard radio- and chemo-therapy protocols. If the variation is large, then pretreatment assay to design individualized treatments will be very important and will have the potential to considerably increase cure rates; particularly if those who would have failed a standard protocol can be spared that treatment and given one which their assay results suggest will be more effective for them.

EXAMPLE 2

The Hybrid Spheroid (hs) Assay

To alleviate the problems in the prior art methods, an in vivo-like system, the hs assay suitable for testing primary tumor cells has been developed [Djordjevic B. et al., Acta Oncologica, 2006, 45, 412-420; Djordjevic B. et al., Radiat. Res. 53rd Annual Meeting Program Book p 99 (PS179), Nov. 6-9, 2006, Philadelphia, Pa.; and Djordjevic B. et al., Int J Radiat Oncol Biol Phys 1992; 24(3): 511-518; Lange C. S. et al., Int J Radiat Oncol Biol Phys 1992, 24(3): 511-518; Djordjevic, B. et al., Cancer Invest 1991, 9(5): 505-512; Djordjevic B. et al., Cancer Invest. 1993, 11(3): 291-298; Djordjevic B. et al., Acta Oncologica 1998, 37: 735-739; Djordjevic B. et al., Radiat Res 1998, 150:275-282; Djordjevic B. et al., Indian J Exper Biol 2004, 42: 443-447] (see below). The system exhibits a much higher PE, ~0.5-2% [Djordjevic B. et al., Acta Oncologica, 2006, 45, 412-420], with almost all samples producing sufficient colonies for assay [Djordjevic B. et al., Acta Oncologica, 2006, 45, 412-420; Djordjevic B. et al., Radiat. Res. 53rd Annual Meeting Program Book p 99 (PS179), Nov. 6-9, 2006, Philadelphia, Pa.; Djordjevic B. et al., Radiat Res 1998, 150:275-282; Djordjevic B. et al., Indian J Exper Biol 2004, 42: 443-447]. This PE is consistent with the hypothesis that what formed colonies in vitro were the cancer stem cells (CSCs). Furthermore, in the hybrid spheroid system, cells are enveloped in a three-dimensional (3D) agglomerate of cells, initially providing an analog of the stem cell niche, and after treatment exhibiting all the mutual influences on survival. This is important, as it is becoming clear that the initial growth of CSCs depends on having an appropriate niche (plating of 40,000 single tumor cells fails to yield even one colony when ~400 would have been expected from the hs PE), and that the survival of tumor cells and the functionality of various tissues surrounding tumors are determined not only by the direct impact of inactivating agents, but also by the now well recognized Bystander Effect (BE) (see [Azzam E. I. et al., Hum Exp Toxicol 2004, 23: 61-65; Iyer R. et al., Arch Biochem Biophys 2000, 376: 14-25; Seymour C. B. et al., Radiat Res 2000, 153: 508-511; Ishii K. et al., Int J Radiat Biol 1996, 69: 291-299; Bishayee A. et al., Radiat Res 1999, 152: 88-97; Azzam E. I. et al., Radiat Res 1998, 150: 497-504; Djordjevic B., BioEssays 2000, 22: 286-29]).

Hybrid spheroids were first shown to form from mixtures of HeLa test cells and supralethally irradiated HeLa feeder cells [Djordjevic B. et al., Int J Radiat Oncol Biol Phys 1992; 24(3): 511-518]. Using this system with test cells directly from human tumor surgical samples (breast, colon, cervix, head and neck, etc.) it was shown that the PE was considerably higher than that in other clonogenicity based putative predictive assays for patient tumor radiosensitivity [Lange C. S. et al., Int J Radiat Oncol Biol Phys 1992, 24(3): 511-518]. Unlike monolayer assays, this system appeared to maintain the G0 fraction in chemosensitivity assays [Djordjevic, B. et al., Cancer Invest 1991, 9(5): 505-512; Djordjevic B. et al., Cancer Invest. 1993, 11(3): 291-298], and was the only one reliably to provide radiation survival curves [Djordjevic B. et al., Acta Oncologica, 2006, 45, 412-420; Djordjevic B. et al., Radiat. Res. 53rd Annual Meeting Program Book p 99 (PS179), Nov. 6-9, 2006, Philadelphia, Pa.; Djordjevic B. et al., Int J Radiat Oncol Biol Phys 1992; 24(3): 511-518; Lange C. S. et al., Int J Radiat Oncol Biol Phys 1992, 24(3): 511-518; Djordjevic B. et al., Radiat Res 1998, 150:275-282; Djordjevic B. et al., Indian J Exper Biol 2004, 42: 443-447]. Moreover, the radiosensitivity of HeLa test cells (as a model) to each daily dose fraction was shown to increase exponentially with increasing number of fractions [Djordjevic B. et al., Radiat Res 1998, 150:275-282], rather than remain constant, as previously assumed. This was shown to be a form of BE [Djordjevic B., BioEssays 2000, 22: 286-290]. Test cell contact with supralethally irradiated feeder cells produces an artifactually large BE effect [Djordjevic B., BioEssays 2000, 22: 286-290]. The finding that pure fibroblast spheroids rapidly shrink and lose clonogenicity exponentially [Djordjevic B. et al., *Acta Oncologica*, 2006, 45, 412-420; Djordjevic B. et al., *Radiat Res* 1998, 150:275-282; Djordjevic B. et al., *Indian J Exper Biol* 2004, 42: 443-447] lead to the use of fibroblasts as feeder cells in hybrid spheroids, with the advantage that the fibroblasts also block the growth of stromal fibroblasts (which could otherwise overgrow the culture). The results of some of our most recent studies using HeLa test cells (as a repeatable standard) and fresh cervical cancer cells are presented below.

Growth Characteristics of Spheroids Composed of Fibroblasts or HeLa Cells:

In order to verify the utility of AG1522 fibroblasts as (non-growing) feeder cells in hybrid spheroids, spheroids composed entirely of either live fibroblasts, or of supralethally irradiated fibroblasts, were incubated in suspension over a period of several days, and the growth (change in volume of spheroids) measured (by light microscopy). The results in FIG. 1 show that both types of spheroids shrank to about 10-20% of their original size within three days (day four after creation), after which, they remain the same reduced size for the rest of the period of observation (up to two weeks). In contrast, pure spheroids of HeLa cells grow, increasing in size (volume) by an order of magnitude over a six day period. The latter is consistent with the previously reported Gompertzian growth of these cells in spheroids [Djordjevic B. et al., *Acta Oncologica*, 2006, 45, 412-420; Djordjevic B. et al., *Radiat. Res.* 53rd Annual Meeting Program Book p 99 (PS179), Nov. 6-9, 2006, Philadelphia, Pa.; Djordjevic B. et al., *Radiat Res* 1998, 150:275-282; Djordjevic B. et al., *Indian J Exper Biol* 2004, 42: 443-447].

Figure 2:
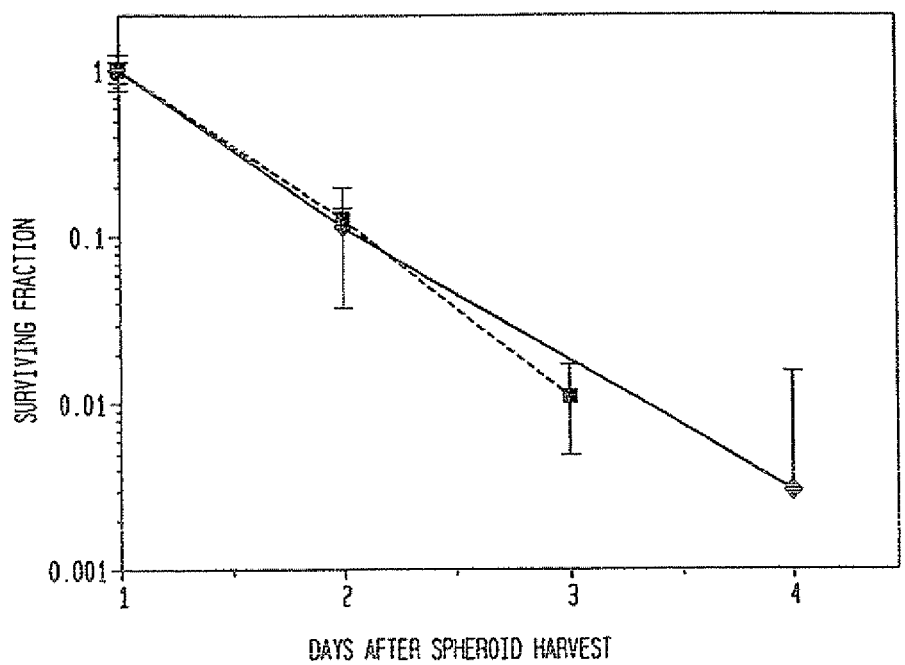
FIG. 2. The loss of clonogenic AG1522 fibroblasts maintained in spheroids. The two curves show the rapid loss of clonogenic fibroblasts in: (1) floating hybrid spheroids with irradiated HeLa feeder cells (squares) and (2) in floating pure spheroids (diamonds). Within three days after harvest, only about 1% of fibroblasts remain clono-genic; within four days <3 per 1,000 remain clonogenic. In both cases, the spheroids were trypsinized before plating for colony formation [Puck T. T. et al., *J Exp Med* 1956, 103: 653-66].

Loss of Fibroblast Clonogenicity in Spheroids in Suspension:

FIG. 2 shows the rapid loss of clonogenic AG1522 fibroblasts in either floating hybrid spheroids with irradiated HeLa feeder cells or in floating pure spheroids [Djordjevic B. et al., *Acta Oncologica*, 2006, 45, 412-420; Djordjevic B. et al., *Radiat. Res.* 53rd Annual Meeting Program Book p 99 (PS179), Nov. 6-9, 2006, Philadelphia, Pa.]. Within three days after harvest, only about 1-2% of fibroblasts remain clonogenic; within four days, <3 per thousand remain clonogenic; extrapolating, within a week <1/10$^6$ remain clonogenic.

The negative growth characteristics (shrinkage and loss of clonogenicity) of spheroids in suspension, composed of fibroblasts (FIGS. 1-2), indicated that when hybrid spheroids grew, it was due to the proliferation of their (HeLa) test cells, not of the AG1522 fibroblast feeder cells. It follows for hybrid spheroids, that fibroblasts did not make a contribution to the growth of (hybrid) spheroids, as further evidenced from the following experiment. Upon termination of the spheroid growth experiment (ten days), resulting spheroids were trypsinized, plated in a tissue culture dish, and stained after a suitable growth period (ten additional days), as detailed in the Methods section. It was found that the only colonies (<99.9%) to grow from these dispersed hybrid spheroids were HeLa cells, even though the spheroids initially consisted predominantly of fibroblasts.

Growth Curves for Hybrid Spheroids with HeLa Test Cells:

96-well plates containing hs which had been irradiated with different doses (and a zero dose control) were followed for spheroid growth over a 2-4 week period. Similar data were obtained for several experiments, so only the data for one experiment are shown here. The growth curves for individual unirradiated hybrid spheroids are shown below. The data for those spheroids whose volume showed an increase (indicating the growth of the HeLa cells), were organized to show the growth graphically. To reduce the congestion, we plotted only those spheroids which did not shrink and disappear.

Figure 3:
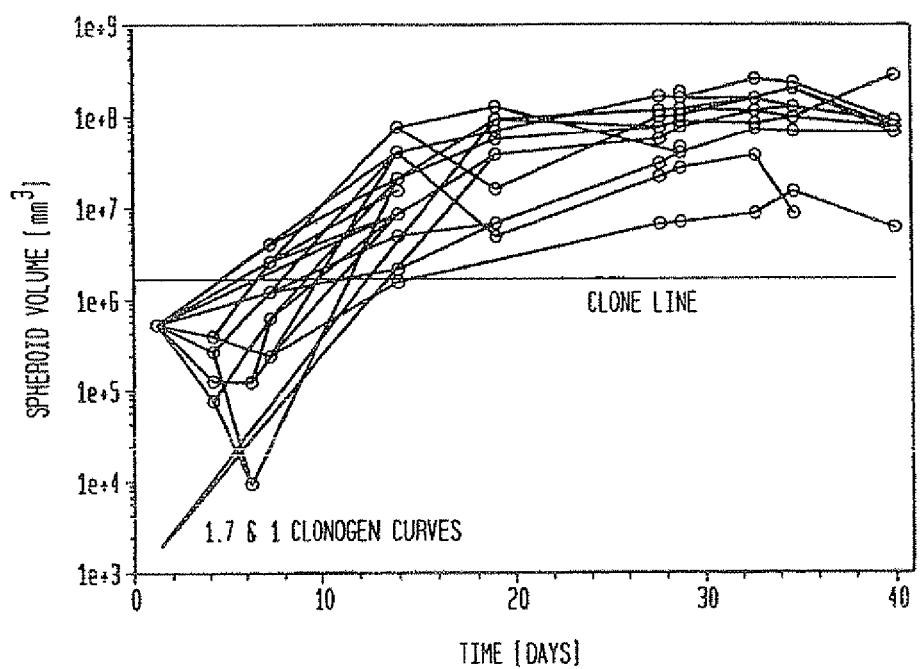
FIG. 3 shows some growth curves for spheroids that grew to a size representing at least one clonogen in the original spheroid. The horizontal "clone line" is the spheroid size corresponding to shrinkage of the original fibroblast spheroid to 20% of its volume and a single clonogen undergoing 10 divisions. Spheroids which shrank and disappeared are not shown. Each line represents the volume of a single spheroid (an average of one per well) over a period of 40 days for the unirradiated spheroids.

FIG. 3 shows some growth curves for spheroids that grew to a size representing at least one clonogen in the original spheroid. The horizontal "clone line" is the spheroid size corresponding to shrinkage of the original fibroblast spheroid to 20% of its volume and a single clonogen undergoing 10 divisions. Spheroids which shrank and disappeared are not shown. Each line represents the volume of a single spheroid (an average of one per well) over a period of 40 days for the unirradiated spheroids.

Figure 4:
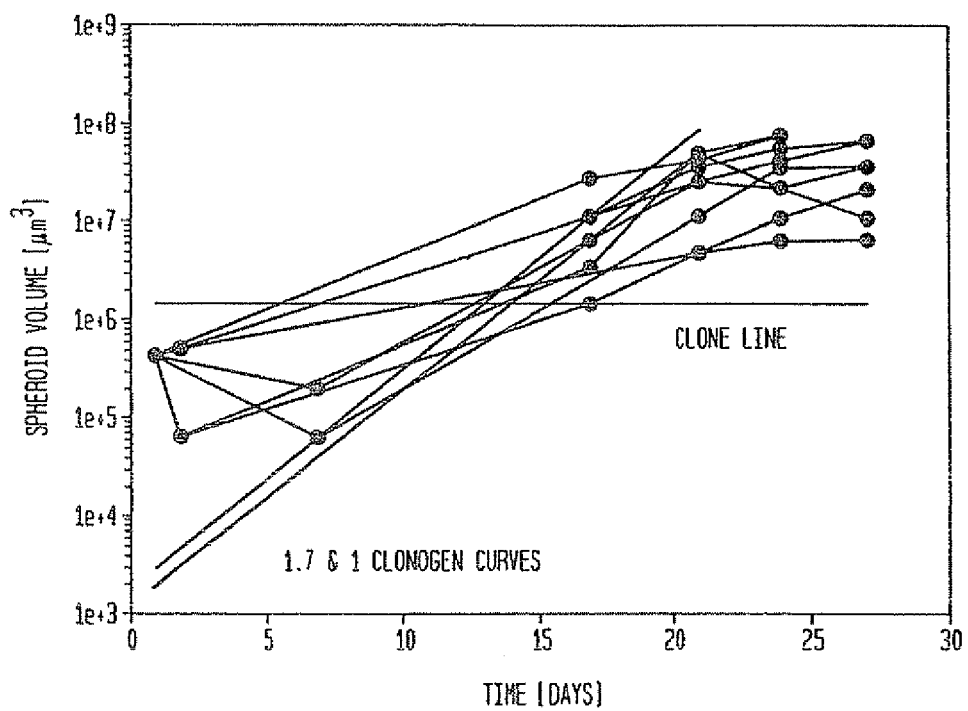
FIG. 4 shows similar growth curves for spheroids irradiated with 3 Gy. The growth rate was consistent with a doubling time for the HeLa cell (or cells) of about 24 hours, similar to that in monolayer culture [Puck T. T. et al., *J Exp Med* 1956, 103: 653-66; Djordjevic B. et al., *Acta Oncologica*, 2006, 45, 412-420].

FIG. 4 shows similar growth curves for spheroids irradiated with 3 Gy. The growth rate was consistent with a doubling time for the HeLa cell (or cells) of about 24 hours, similar to that in monolayer culture [Djordjevic B. et al., *Acta Oncologica*, 2006, 45, 412-420; Djordjevic B. et al., *Radiat. Res.* 53rd Annual Meeting Program Book p 99 (PS179), Nov. 6-9, 2006, Philadelphia, Pa.].

Figure 5:
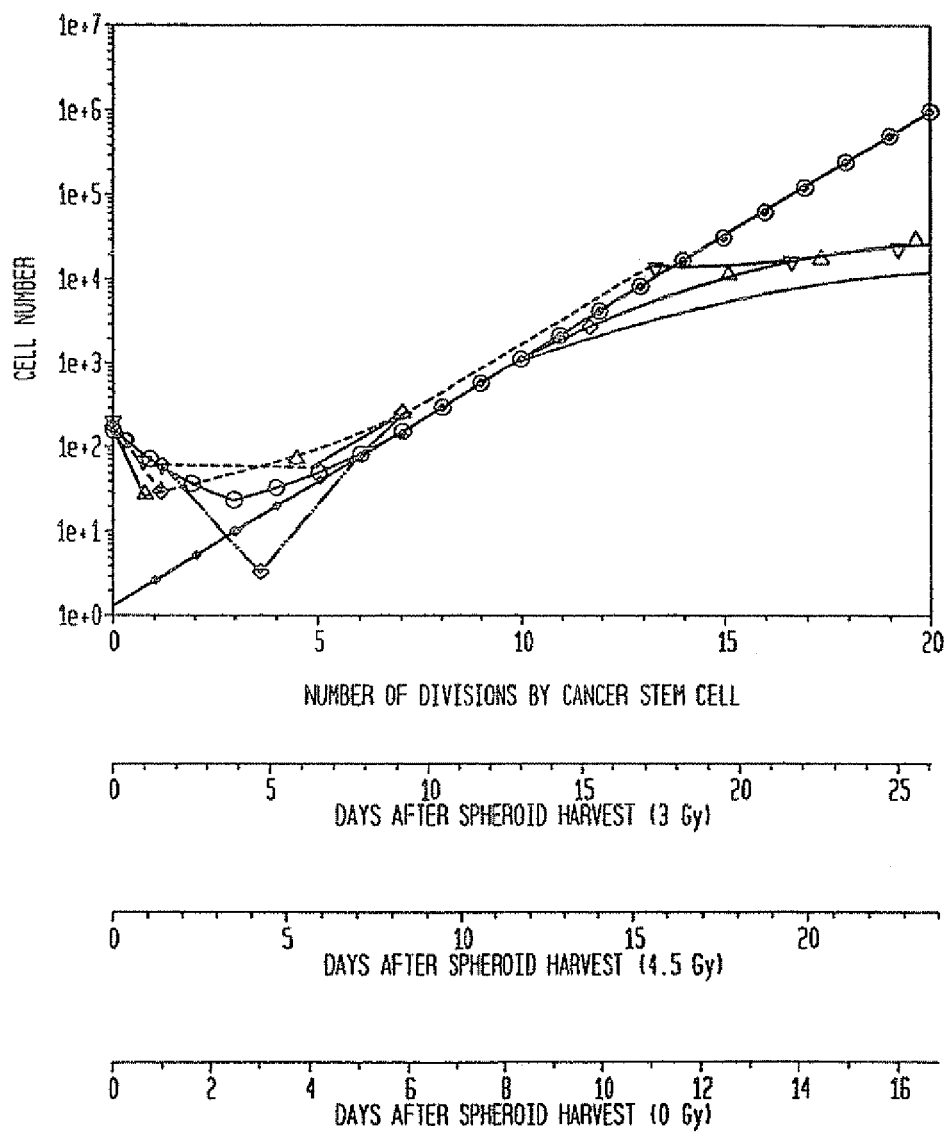
FIG. 5 shows the averaged growth curves for the survivors of 0, 3, and 4.5 Gy doses superimposed on the graph showing the shrinkage of the original fibroblast spheroids and the calculated growth in divisions of a single cancer stem cell (clonogen). The doubling time for all of the survivors is ~28.8 hours.

FIG. 5 shows the averaged growth curves for the survivors of 0, 3, and 4.5 Gy doses superimposed on the graph showing the shrinkage of the original fibroblast spheroids and the calculated growth in divisions of a single cancer stem cell (clonogen). The doubling time for all of the survivors is ~28.8 hours.

Figure 6:
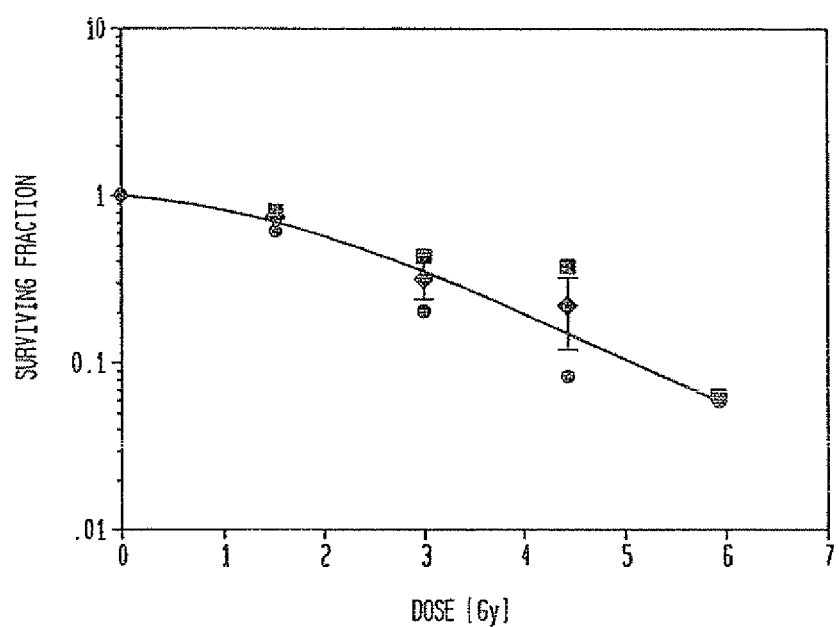
FIG. 6. The squares and circles symbols represent the surviving fractions from two experiments. The line shows the averaged spheroid survival curve. $D_0=1.73\pm0.07$ Gy, $n_{sph}=2.65\pm0.38$, $n_{cell}=1.56\pm0.02$, multiplicity=$n_{sph}/n_{cell}=1.7\pm0.24$.

Survival Curves of X-Irradiated Hybrid Spheroids Maintained in Suspension:

Of the unirradiated spheroids, 55% (42/77) contained ≥1 clonogen. With increasing dose, the fraction of spheroids containing surviving clonogens decreased. The results from several experiments were combined to yield the survival curves shown in FIG. 6 (surviving fraction of spheroids at each dose relative to that for unirradiated spheroids, and when corrected for multiplicity, yielding single cell survival curves).

Comparison of similarly derived curves from spheroids composed of supralethally irradiated (20 Gy) fibroblast feeder cells vs unirradiated fibroblast feeder cells, yielded significantly different curves, with the former steeper by a factor of 1.54±0.13, demonstrating a Bystander Effect. Thus, the use of irradiated feeder cells carries with it the problem of a Bystander effect on the test cells, while the use of unirradiated fibroblasts as feeder cells, which will not proliferate when in 3-D contact as in spheroids, avoids this problem.

Growth of Human Cervical Carcinoma Cells Taken Directly from Tumor Surgical Samples in Hybrid Spheroids:

Cervical carcinoma cells, released from fresh tumor surgical samples by collagenase digestion, produced no colonies when 4×10 cells were plated into tissue culture Petri 4 dishes (PE<2.5×10$^{-5}$). However, when mixed 5.5% tumor cells, 94.5% AG1522 fibroblasts, and allowed to form hs which were harvested and placed, an average of 1 hs/well, in Corning Ultra-Low Attachment 96-well plates, some tumor cells were clonogenic and grew >1000-fold. Two sizes of hs were selected: those initially 88-105 μm in diameter (134 cells), and those initially 105-125 μm diameter (340 cells). Four plates of the former produced a total of 10/290 clones/spheroids (2/96, 2/72, 3/65, 3/57) so 3.69±0.65% grew to be larger than the size corresponding to the growth of a clonogen, yielding a PE=0.50±0.09%. For 105-125 μm hs: 3 plates produced 11/159 clones/spheroids (6/62, 3/49, 2/48) so 6.66±1.32% contained at least one clonogen. These larger hs initially contained 2.54 times more cells than in the smaller hs, yielding a PE=0.35±0.07%.

Poisson Distribution Correction for Number of Clonogens/Spheroid:

There is no need to correct for the Poisson distribution of clonogens/spheroid for the small spheroids (the correction is ~0.01%). The large spheroids, having a larger number of test cells/spheroid, require a correction. This correction, a factor of 2.14, increases the PE for cervical cancer cells in the 105-125 μm spheroids from 0.35±0.07% to 0.76±0.15%. This value is significantly higher than the 0.50±0.09% for these cells in the smaller spheroids (p<0.005).

Thus, we have created a system which can provide a tumor model for an individual patient. 3.7±0.7% of the small (88-105 μm) spheroids and 6.7±1.3% of the large (105-125 μm) spheroids contained tumor clonogens which grew. Since 5.5% of the initial cells in the spheroids were from the tumor, this corresponds to plating efficiencies of cervical carcinoma cells of 0.50±0.09% in the small spheroids and 0.76±0.15% in the large spheroids (or 2.5 times these PEs if only 40% of tumor sample cells are indeed tumor, i.e., 1.25±0.23% and 1.90±0.38%). Both of these results are higher than, the PE of 0.1% reported for the Courtney-Mills method [West C. M. L. et al., *Br J Cancer* 1997, 76: 1184-1190], and with hybrid spheroids, all of the colonies were tumor cells, not fibroblasts [Djordjevic B. et al., *Acta Oncologica*, 2006, 45, 412-420; Djordjevic B. et al., *Radiat. Res. 53rd Annual Meeting Program Book* p 99 (PS179), Nov. 6-9, 2006, Philadelphia, Pa.; Djordjevic B. et al., Int J Radiat Oncol Biol Phys 1992; 24(3): 511-518; Lange C. S. et al., Int J Radiat Oncol Biol Phys 1992, 24(3): 511-518; Djordjevic, B. et al., *Cancer Invest* 1991, 9(5): 505-512; Djordjevic B. et al., Cancer Invest. 1993, 11(3): 291-298; Djordjevic B. et al., Acta Oncologica 1998, 37: 735-739; Djordjevic B. et al., *Radiat Res* 1998, 150:275-282; Djordjevic B. et al., *Indian J Exper Biol* 2004, 42: 443-447].

What is claimed is:

1. A method for treating a cancer patient according to an assay of the patient's cancer stem cell (CSC) sensitivity, the method for treating comprising:
    measuring a proliferative ability of the CSCs in the presence and absence of a drug or treatment, the method for measuring comprising the steps of:
    obtaining a single cell suspension containing stem cells from the patient's tumor, engulfing the stem cell in a spheroid of fibroblast,
    detecting those spheroids within which the stem cell has grown at least 10 divisions to show the presence of cancer stem cells,
    assaying the growth of the single cancer stem cell in the spheroids in suspension in the presence and absence of the drug or treatment, and
    providing the drug or treatment to the patient if there is a decrease in the fraction of cancer stem cell growth in the presence of the drug or treatment compared with control.

2. A method for a drug, a combination of drugs or a treatment development for cancer in a patient, wherein the effects of the drug, combination of drugs and/or treatments is/are determined on the patient's CSCs, comprising:
    obtaining single cell suspension of cancerous tumor cells from the patient;
    engulfing the cells at an average of about one CSC per spheroid of fibroblasts;
    detecting those spheroids that have grown at least 10 divisions to show the presence of CSCs; and
    assaying the effect(s) of the drug, combination of drugs or treatment on the growth of CSC spheroids.

* * * * *